United States Patent [19]

Inoue et al.

[11] 4,127,654
[45] Nov. 28, 1978

[54] COMPOSITIONS AND METHODS CONTAINING BETA SUBSTITUTED ALLYL ALCOHOLS, SULFURIC ACID ESTERS THEREOF, PHOSPHORIC ACID ESTERS THEREOF, ALKANOYL ESTERS THEREOF AND ALKYLENE OXIDE ETHERS THEREOF

[75] Inventors: Shigeo Inoue, Miyashiro; Norioki Miyamoto, Sakura; Haruo Shimizu, Funabashi, all of Japan

[73] Assignee: Kao Soap Co., Ltd., Tokyo, Japan

[21] Appl. No.: 720,376

[22] Filed: Sep. 3, 1976

[30] Foreign Application Priority Data

Sep. 12, 1975 [JP] Japan ............................. 50-110543

[51] Int. Cl.$^2$ ................... A01N 9/36; A61K 31/66; A61L 13/00
[52] U.S. Cl. ..................................... 424/216; 252/9; 252/106; 424/70; 424/303; 424/335; 424/337; 424/358; 424/361
[58] Field of Search ............. 424/335, 337, 358, 216, 424/303; 260/609, 607 AL

[56] References Cited

U.S. PATENT DOCUMENTS

| 3,000,779 | 9/1961 | Goodhue et al. ............. 424/337 |
| 3,078,298 | 2/1913 | Gregory et al. ............. 560/150 |
| 3,103,464 | 9/1963 | Larson et al. ............. 424/335 |
| 3,137,615 | 6/1964 | Ichikawa et al. ............. 424/335 X |
| 3,541,119 | 11/1970 | Richter et al. ............. 560/150 |
| 3,655,772 | 4/1972 | Chang et al. ............. 424/337 X |

FOREIGN PATENT DOCUMENTS 2,130,775  12/1972  Fed. Rep. of Germany ........... 424/335

Primary Examiner—Dale R. Ore
Attorney, Agent, or Firm—Blanchard, Flynn, Thiel, Boutell & Tanis

[57] ABSTRACT

Compounds having the formula $$R-X-CH=CH_2-CH_2O-Y \qquad (I)$$

wherein R is alkyl or alkenyl containing one to 20 carbon atoms, X is S, SO or SO$_2$ and Y is hydrogen, alkanoyl containing 2 to 20 carbon atoms or alkenoyl containing 3 to 20 carbon atoms, SO$_3$M or PO$_3$M$_2$, wherein M is hydrogen, an alkali metal or an alkaline earth metal, or an oxyalkylene group having 1–20 ethylene oxide units or propylene oxide units, are incorporated as a preservative or anti-microbial agent, in compositions that are subject to deterioration by the action of microorganisms, excluding food and medicines.

12 Claims, No Drawings

COMPOSITIONS AND METHODS CONTAINING BETA SUBSTITUTED ALLYL ALCOHOLS, SULFURIC ACID ESTERS THEREOF, PHOSPHORIC ACID ESTERS THEREOF, ALKANOYL ESTERS THEREOF AND ALKYLENE OXIDE ETHERS THEREOF

CROSS-REFERENCE TO RELATED APPLICATIONS

This application is related to U.S. Ser. No. 699,324, filed June 24, 1976, and U.S. Ser. No. 702,405, filed July 6, 1976, both now abandoned, the entire contents of which are incorporated herein by reference.

The present invention relates to compositions, excluding foods and medicines, containing bactericidal/disinfecting agents or antifungal/antiseptic agents. More particularly, the present invention provides compositions containing antimicrobial agents comprising compounds of the formula (I):

$$R-X-CH=CH-CH_2O-Y \quad (I)$$

wherein R is alkyl or alkenyl containing one to 20 carbon atoms, X is S, SO or $SO_2$ and Y is hydrogen, an alkanoyl (alkyl carbonyl) having 2 to 20 carbon atoms or alkenoyl (alkenyl carbonyl) having 3 to 20 carbon atoms, $SO_2M$ or $PO_3M_2$, wherein M is hydrogen, an alkali metal or an alkaline earth metal, or an oxyalkylene group having 1 to 20 ethylene oxide units or propylene oxide units.

The inventors have often used various known antimicrobial agents as bactericidal, antifungal or antiseptic agents. However, many problems have been encountered in the use of them. Many known antimicrobial agents were developed for the essential purpose of exhibiting antimicrobial activities, but even the agents which were considered to have a very wide scope of application at the time of the development thereof are unsuitable for this use in various new systems which have been developed rapidly.

For example, for preventing microbial deterioration of cosmetics, domestic sundries, etc., there have been added thereto benzoic acid, aromatic phenolic antimicrobial agents such as salicylic acid or alkali metal salts thereof, p-hydroxybenzoic acid esters, p-isopropyl-o-methylphenol, o-phenylphenol and invert soaps such as alkylbenzyldimethylammonium halides. First, the degree of antimicrobial activity of the agent was tested, without paying any regard to physicochemical properties of the systems. Then tests on the compatibility of the agent with the systems and the stability thereof in the systems were carried out for a long time period. Moreover, in these tests, each agent must be tested as regards various items and each experiment requires a long period of time. The results of the tests usually showed that only a very small number of agents were useful in a particular system. The same procedures must be repeated for each different system. Thus, much labor and time is needed to complete the tests. This has been a great barrier to the development of commercial products. Further, the known antimicrobial agents have been used widely for a long period of time and, consequently, resistant bacteria have appeared remarkably and the control of microbial contamination in manufacturing plants and the products produced thereat is very difficult.

Thus, the development of new agents having both excellent antimicrobial activities and excellent physicochemical properties for use as an ingredient of the base of various compositions has been demanded.

We have found that compounds of the above formula (I) have both excellent antimicrobial activities and excellent physicochemical properties so that they can be used as an ingredient of the base of various compositions.

The compounds of formula (I) include the following typical examples:

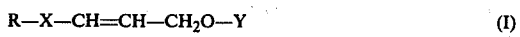

1. β-Alkylsulfenylallyl alcohols
   $n\text{-}C_{12}H_{25}-S-CH=CH-CH_2OH$
   (m.p. 50–51° C)

2. β-Alkylsulfinylallyl alcohols
   $n\text{-}C_{12}H_{25}-\underset{\underset{\text{O}}{\|}}{S}-CH=CH-CH_2OH$
   ($n_D^{20}$ 1.5231)

3. β-Alkylsulfonylallyl alcohols
   $n\text{-}C_{12}H_{25}-\underset{\underset{\text{O}}{\|}}{\overset{\overset{\text{O}}{\|}}{S}}-CH=CH-CH_2OH$
   (m.p. 95–97° C)

4. β-Alkylsulfenylallyl alcohol sulfuric acid esters
   $n\text{-}C_{12}H_{25}-S-CH=CH-CH_2OSO_3Na$
   (m.p. 83–84° C)

5. β-Alkylsulfinylallyl alcohol sulfuric acid esters
   $n\text{-}C_{12}H_{25}-\underset{\underset{\text{O}}{\|}}{S}-CH=CH-CH_2OSO_3Na$
   (m.p. 72–73° C)

6. β-Alkylsulfonylallyl alcohol sulfuric acid esters
   $n\text{-}C_{12}H_{25}-\underset{\underset{\text{O}}{\|}}{\overset{\overset{\text{O}}{\|}}{S}}-CH=CH_2OSO_3Na$
   (m.p. 102–103° C)

7. β-Alkylsulfenylallyl alcohol phosphoric acid esters
   $n\text{-}C_{12}H_{25}-S-CH=CH-CH_2OPO_3Na_2$
   ($n_D^{20}$ 1.5103)

8. β-Alkylsulfinylallyl alcohol phosphoric acid esters
   $n\text{-}C_{12}H_{25}-\underset{\underset{\text{O}}{\|}}{S}-CH=CH-CH_2OPO_3Na_2$
   ($n_D^{20}$ 1.5204)

9. β-Alkylsulfonylallyl alcohol phosphoric acid esters
   $n\text{-}C_{12}H_{25}-\underset{\underset{\text{O}}{\|}}{\overset{\overset{\text{O}}{\|}}{S}}-CH=CH-CH_2OPO_3Na_2$
   ($n_D^{20}$ 1.5134)

10. β-Alkylsulfenylallyl alcohol alkanoyl esters
    $n\text{-}C_{12}H_{25}-S-CH=CH-CH_2OCOCH_3$
    ($n_D^{20}$ 1.5083)

11. β-Alkylsulfinylallyl alcohol alkanoyl esters
    $n\text{-}C_{12}H_{25}-\underset{\underset{\text{O}}{\|}}{S}-CH=CH-CH_2OCOCH_3$
    ($n_D^{20}$ 1.5263)

12. β-Alkylsulfonylallyl alcohol alkanoyl esters
    $n\text{-}C_{12}H_{25}-\underset{\underset{\text{O}}{\|}}{\overset{\overset{\text{O}}{\|}}{S}}-CH=CH-CH_2OCOCH_3$
    ($n_D^{20}$ 1.5202)

13. Polyoxyethylene-β-alkylsulfenylallyl alcohol ethers
    $n\text{-}C_{12}H_{25}-S-CH=CH-CH_2O(CH_2CH_2O)_{15}H$
    ($n_D^{20}$ 1.5362)

14. Polyoxyethylene-β-alkylsulfinylallyl alcohol ethers
    $n\text{-}C_{12}H_{25}-\underset{\underset{\text{O}}{\|}}{S}-CH=CH-CH_2O(CH_2CH_2O)_{15}H$
    ($n_D^{20}$ 1.5248)

15. Polyoxyethylene-β-alkylsulfonylallyl alcohol ethers

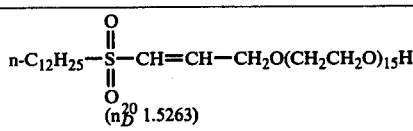

The compounds of formula (I) of the present invention can be prepared, for example, by the following methods:

(a) A mercaptan of the formula (II):

wherein R has the same meaning as defined above, is reacted with propargyl alcohol in the presence of an alkoxide in an alcohol, or in the presence of an alkali metal hydroxide in aqueous solution to obtain a compound of formula (I), wherein X is S and Y is hydrogen (Japanese Patent application No. 24550/1975).

(b) The aliphatic alcohol obtained in (a) is reacted with fatty acids or fatty acid halides of 2 to 20 carbon atoms in the presence of an acidic or basic catalyst to obtain esters of the above formula (I) wherein X is S and Y is an alkanoyl of 2 to 20 carbon atoms or alkenoyl group of 3 to 20 carbon atoms.

(c) The aliphatic alcohol obtained in (a) is sulfated with a sulfating agent such as sulfuric acid anhydride, concentrated sulfuric acid or chlorosulfuric acid to obtain a compound of formula (I) wherein X is S and Y is $SO_3M$, M having the same meaning as defined above.

(d) The aliphatic alcohol obtained in (a) is phosphorized with a phosphorizing agent such as phosphorus pentoxide or a phosphorus oxyhalide to obtain a compound of formula (I) wherein X is S and Y is $PO_3M_2$, M having the same meaning as defined above.

(e) The aliphatic alcohol obtained in (a) is reacted with an alkylene oxide in the presence of a basic catalyst to obtain a compound of formula (I) wherein X is S and Y is an oxyalkylene group containing 1 to 20 ethylene oxide or propylene oxide units.

(f) The compounds obtained in (a)–(e) are oxidized with an inorganic or organic peroxide such as sodium metaperiodate, hydrogen peroxide, m-chloroperbenzoic acid, perbenzoic acid or peracetic acid to obtain the corresponding compounds of formula (I) wherein X is SO or $SO_2$.

The compounds of formula (I) of the present invention have both antimicrobial activities and physicochemical properties that make them suitable for use in the bases of cosmetics such as creams, lotions, shampoos and rinses; as detergents; or as chemical products.

Above compounds 1., 2. and 3. have the effect of stabilizing the foams of detergents such as kitchen detergents, shampoos and rinses; the effect of stabilizing emulsions; and a good compatibility with compositions containing aliphatic alcohols as a principal ingredient, like aliphatic monohydric alcohols.

Compounds 4., 5. and 6. have an excellent surfactant activity like that of sodium lauryl sulfate, etc. Although their antimicrobial activities are inferior to those of other compounds of the present invention, they possess excellent surfactant activities and excellent compatibilities with anionic surfactant-containing compositions. They thus possess a unique combination of properties, i.e. surfactant activity and antimicrobial activity, which combination of properties is not observed in other anionic surfactants.

Compounds 7., 8. and 9., particularly the alkali metal salts thereof, are excellent anionic surfactants that also possess antimicrobial activities.

Compounds 10., 11. and 12. are suitable for use as both an oil ingredient and an antiseptic of various emulsions such as cosmetics and shampoos; additives for plastics, fiber smoothing agents, lubricants, paints and printing inks; or oils for metal processing. They can be used also as antiseptics for various chemical products. Further, the higher fatty acid esters are waxy materials and they are excellent antiseptics for emulsified wax-containing compositions.

Compounds 13., 14. and 15. have nonionic surfactant activity and exhibit the wide range of effects of nonionic surfactants such as wetting, emulsifying, deterging and solubilizing actions. Their properties are very close to those of conventional polyoxyethylene adducts which are typical nonionic surfactants. Thus, they can be used widely as surfactants and as antiseptics for cosmetics, domestic sundries and various chemical products.

The amount of the compound of formula (I) of the present invention that is added to the system in which it is to be incorporated varies greatly depending on the purpose or purposes that it is intended to serve. The amount thereof to be added when it is employed for only antimicrobial activity, for example, antiseptic activity, as expected, is greatly different from the amount that is added when it is employed as both a base and as an antimicrobial agent.

When only an antimicrobial effect of the compounds of the present invention is desired, it is preferred to use about 0.05 to 5 wt. % of compounds of formula (I) wherein R is alkyl or alkenyl of 1 to 8 carbon atoms, preferably 2 to 8 carbon atoms, most preferably 4 to 8 carbon atoms.

On the other hand, when the compound is added both as a base of the system and as an antimicrobial agent, it is preferred to use about 1 to 25% of compounds of formula (I) wherein R is alkyl or alkenyl of 6 to 20 carbon atoms, preferably 6 to 18 carbon atoms, most preferably 8 to 16 carbon atoms.

However, it is to be noted that amount of the compound of the present invention can be varied according to conditions, since the amount depends upon the properties of the system, its expected action as a base and its antimicrobial effect.

According to this invention, the compound of the formula (I) may be incorporated into compositions as shown below.

A liquid detergent composition consists essentially of 10 to 50% by weight, preferably 15 to 30%, of one or more surfactants selected from anionic surfactants, nonionic surfactants and zwitter-ionic surfactants, 1 to 15% by weight, preferably 3 to 10%, of a stabilizer and the balance of water. As the anionic surfactants, there may be used a alkali metal salts and alkanol amine salts, for example alkylbenzenesulfonate having alkyl group of 10 to 16 carbon atoms, alkanesulfonate having 10 to 20 carbon atoms, alkyl sulfate having 10 to 20 carbon atoms and polyoxyethylenealkylethersulfate having alkyl of 10 to 20 carbon atoms and 1 to 20 ethylene oxide units. As the nonionic surfactants, there may be used polyoxyethylenealkylether having alkyl of 10 to 20 carbon atoms and 5 to 20 ethyleneoxide units, polyoxyethylenealkylphenylether having alkyl of 8 to 12 carbon atoms and 5 to 20 ethylene oxide units and fatty acid alkylolamide derived from a fatty acid of 10 to 20 carbon atoms. As the zwitter-ionic surfactants, there may be used betain, sulfobetain, an imidazol-type surfactant having a long chain alkyl group of 10 to 20 carbon atoms. As the stabilizer, there may be used for example lower alcohols of 1 to 4 carbon atoms such as ethanol and propanol and glycols such as ethyleneglycol and propyleneglycol, urea and aromatic sulfonates such as toluene sulfonate and xylene sulfonate.

An oil-in-water emulsion cutting oil composition consists essentially of 85 to 95% by weight of liquid paraffin and 5 to 15% by weight of one or more organic surfactants selected from anionic surfactants and nonionic surfactants as defined above.

A cosmetic composition consists essentially of 10 to 70% by weight, preferably 15 to 50%, of oil or fat component selected from liquid paraffin and vegetable oil such as olive oil, castor oil, lanolin alcohol, lanolin ester and fatty acid ester, 3 to 40% by weight, preferably 10 to 30%, of one or more organic surfactants selected from anionic surfactants such as fatty acid salts (soap), alkylsulfate of 10 to 20 carbon atoms, and polyoxyethylenealkylethersulfate having alkyl of 10 to 20 carbon atoms and 1 to 10 ethylene oxide units and nonionic surfactants such as polyoxyethylenealkylether having alkyl of 10 to 20 carbon atoms and 1 to 10 ethyleneoxide units, fatty acid monoglyceride and sorbitol fatty acid ester, and 10 to 50% by weight, preferably 15 to 40%, of water.

A shampoo composition consists essentially of 5 to 35% by weight, preferably 8 to 20%, of anionic organic surfactants selected from alkyl metal salts and alkanolamine salts of alkylbenzene sulfonate having alkyl of 10 to 16 carbon atoms, those of alkyl sulfate having alkyl of 10 to 20 carbon atoms, those of alkanesulfonate of 10 to 20 carbon atoms, those of alpha-olefinesulfonate of 10 to 20 carbon atoms and those of polyoxyethylenealkylethersulfate having alkyl of 10 to 20 carbon atoms and 1 to 10 ethyleneoxide units, optionally containing nonionic surfactant, zwitter-ionic surfactant, oil and fat component, stabilizer and chelating agent.

The antimicrobial effect of the compound according to this invention is generally greater in order of —S—, —$SO_2$— and —SO— as X of the formula I, however the effect, particularly to mold fungi, is greater in order of —SO—, $SO_2$— and —S—.

The present invention will be further described with reference to the following illustrative examples.

EXAMPLE 1

Active groups and growth inhibition effects on Gram-negative bacteria

The concentrations of the agents in a culture medium required for inhibiting growth of various bacteria were determined by the agar culture medium test method for the agents.

One milliliter of a solution of the agent having a predetermined concentration was taken and placed on a Petri dish. Then, 19 ml of dissolved nutrient agar medium was added thereto. This was stirred to obtain a homogeneous mixture, which was then allowed to cool and thereby solidified. One platinum loopful of a microbial solution which had been adjusted to have a concentration of number of cells of 1,000,000/ml was applied to the surface of the medium. After the culture was held in a constant temperature room at 30° C. for 48 hours, the minimum growth inhibition concentration of the agent in the medium was determined from degree of growth to the microbes.

The symbols employed in the following tables have the following meanings:

+: Microbes grew. A growth inhibition effect was not recognized.

±: Microbes grew slightly. A moderate growth inhibition effect was recognized.

—: The growth was inhibited completely. A strong growth inhibition effect was recognized.

The results were as shown in Table 1.

Table 1

| Active compound | Minimum growth inhibition conc. (ppm) | | | | | |
|---|---|---|---|---|---|---|
| | Staphylococcus aureus | | | Bacillus subtilis | | |
| | 1000 | 500 | 100 | 1000 | 500 | 100 |
| n-$C_4H_9$—S—CH=CH—$CH_2$OH | — | + | + | — | + | + |
| 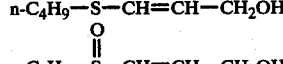 n-$C_4H_9$—S(=O)—CH=CH—$CH_2$OH | — | — | — | — | — | — |
| 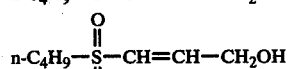 n-$C_4H_9$—S(=O)—CH=CH—$CH_2$OH | — | — | + | — | ± | + |
| 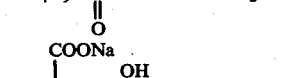 n-$C_4H_9$—$SO_2$—CH=CH—$CH_2$OH | | | | | | |
| 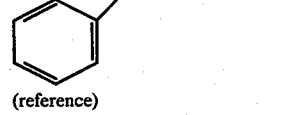 (reference) COONa, OH on benzene ring | — | + | + | — | + | + |
| HO—C6H4—$CO_2C_2H_5$ (reference) | — | — | + | — | ± | + |

EXAMPLE 2

Active groups and growth inhibition effects on Gramnegative bacteria

The results of the tests, carried out in the same manner as described in Example 1, were as shown in Table 2.

EXAMPLE 3

Alkyl chain length and growth inhibition effects on bacteria

The results of the tests, carried out in the same manner as described in Example 1, were as shown in Table 3.

EXAMPLE 4

Growth inhibition effects of various compounds on bacteria

The results of the tests, carried out in the same manner as described in Example 1, were as shown in Table 4.

Table 2

| Active compound | Minimum growth inhibition conc. (ppm) | | | | | | | | |
|---|---|---|---|---|---|---|---|---|---|
| | Escherichia coli | | | Proteus vulgaris | | | Pseudomonas aeruginosa | | |
| | 1000 | 500 | 100 | 1000 | 500 | 100 | 1000 | 500 | 100 |
| n-C$_4$H$_9$—S—CH=CH—CH$_2$OH | ± | + | + | + | + | + | + | + | + |
| n-C$_4$H$_9$—S(=O)—CH=CH—CH$_2$OH | − | ± | + | − | − | + | − | + | + |
| n-C$_4$H$_9$—S(O)$_2$—CH=CH—CH$_2$OH | − | + | + | − | + | + | + | + | + |
| Sodium salicylate (COONa, OH on benzene) (reference) | ± | + | + | ± | + | + | + | + | + |
| HO—C$_6$H$_4$—CO$_2$C$_2$H$_5$ (reference) | − | ± | + | − | − | + | ± | + | + |

Table 3

| Active compound | Minimum growth inhibition conc. (ppm) | | | | | | | | | | | | | | |
|---|---|---|---|---|---|---|---|---|---|---|---|---|---|---|---|
| | Staphylococcus aureus | | | Bacillus subtilis | | | Escherichia coli | | | Proteus vulgaris | | | Pseudomonas aeruginosa | | |
| | 1000 | 500 | 100 | 1000 | 500 | 100 | 1000 | 500 | 100 | 1000 | 500 | 100 | 1000 | 500 | 100 |
| n-C$_4$H$_9$—S(=O)—CH=CH—CH$_2$OH | − | − | − | − | − | − | ± | + | − | − | + | − | + | + | + |
| n-C$_6$H$_{13}$—S(=O)—CH=CH—CH$_2$OH | − | − | − | − | − | − | + | + | − | + | + | ± | + | + | + |
| n-C$_8$H$_{17}$—S(=O)—CH=CH—CH$_2$OH | − | − | − | + | + | + | + | + | + | + | + | + | + | + | + |
| n-C$_{10}$H$_{21}$—S(=O)—CH=CH—CH$_2$OH | − | − | + | − | + | + | + | + | + | + | + | + | + | + | + |
| n-C$_{12}$H$_{25}$—S(=O)—CH=CH—CH$_2$OH | − | − | − | − | − | − | − | − | + | − | + | + | + | + | + |
| n-C$_{14}$H$_{29}$—S(=O)—CH=CH—CH$_2$OH | − | − | − | − | − | − | + | + | + | + | + | + | + | + | + |
| Sodium salicylate (reference) | − | + | + | − | + | + | ± | + | + | ± | + | + | + | + | + |
| HO—C$_6$H$_4$—CO$_2$C$_2$H$_5$ (reference) | − | − | + | − | ± | + | − | ± | + | − | − | + | ± | + | + |

Table 4

| Active compound | Staphylococcus aureus | | | Bacillus subtilis | | | Escherichia coli | | | Proteus vulgaris | | | Pseudomonas aeruginosa | | |
|---|---|---|---|---|---|---|---|---|---|---|---|---|---|---|---|
| | 1000 | 500 | 100 | 1000 | 500 | 100 | 1000 | 500 | 100 | 1000 | 500 | 100 | 1000 | 500 | 100 |
| | Minimum Growth inhibition conc. (ppm) | | | | | | | | | | | | | | |
| n-C$_4$H$_9$—S(=O)—CH=CH—CH$_2$OH | − | − | − | − | − | − | − | ± | + | − | − | − | − | + | + |
| n-C$_4$H$_9$—S(=O)—CH=CH—CH$_2$OCOCH$_3$ | − | − | − | − | − | − | ± | − | ± | − | − | − | − | ± | + |
| n-C$_4$H$_9$—S(=O)—CH=CH—CH$_2$OSO$_3$Na | − | − | − | − | − | − | − | + | + | ± | + | + | + | ++ | + |
| n-C$_4$H$_9$—S(=O)—CH=CH—CH$_2$OPO$_3$Na$_2$ | − | − | − | − | − | + | − | + | + | − | + | + | + | + | + |
| n-C$_4$H$_9$—S(=O)—CH=CH—CH$_2$O(CH$_2$CH$_2$O)$_5$H | − | − | + | − | ± | + | ± | ± | + | + | ± | + | ± | + | + |
| (reference) 2-hydroxybenzoic acid, sodium salt (COONa, OH on benzene) | − | − | − | − | − | − | − | − | + | − | − | + | − | + | + |
| (reference) ethyl 4-hydroxybenzoate (HO—C$_6$H$_4$—CO$_2$C$_2$H$_5$) | | | | | | | | | | | | | | | |

EXAMPLE 5

Growth inhibition effects of various compounds on molds and yeasts

The results of the tests, carried out in the same manner as described in Example 1, were as shown in Table 5.

and 2 parts of sodium salts of fatty acids) which had been diluted to a concentration of 1:20 with city water. Three strains of Pseudomonas aeruginosa (IFO 3898, 3919 and 3924) and one strain of Escherichia coli (IFO 3806) were inoculated in the form of a mixed microbial solution of a microbe cell number of $10^8$/ml into the mixture. Shaking culture was effected at a constant Table 5

| | Minimum Growth inhibition conc. (ppm) | | | | | | | | | | | |
|---|---|---|---|---|---|---|---|---|---|---|---|---|
| | Penicillium citrinum | | | Aspergillus niger | | | Trichophyton mentagrophytes | | | Candida albicans | | |
| Active compound | 1000 | 500 | 100 | 1000 | 500 | 100 | 1000 | 500 | 100 | 1000 | 500 | 100 |
| n-$C_8H_{17}$—S—CH=CH—$CH_2$OH | − | + | + | − | + | + | − | − | + | ± | + | + |
| n-$C_8H_{17}$—S(O)—CH=CH—$CH_2$OH | − | − | + | − | − | + | − | − | − | − | − | + |
| n-$C_8H_{17}$—S(O)(O)—CH=CH—$CH_2$OH | − | + | + | − | + | + | − | − | − | − | ± | + |
| n-$C_8H_{17}$—S—CH=CH—$CH_2O(CH_2CH_2O)_2H$ | − | + | + | − | + | + | − | − | + | − | + | + |
| n-$C_8H_{17}$—S(O)—CH=CH—$CH_2O(CH_2CH_2O)_2H$ | − | ± | + | − | + | + | − | − | − | − | ± | + |
| n-$C_8H_{17}$—S(O)(O)—CH=CH—$CH_2O(CH_2CH_2O)_2H$ | − | ± | + | − | ± | + | − | − | − | − | − | + |
| n-$C_8H_{17}$—S(O)(O)—CH=CH—$CH_2OCOCH_3$ | ± | + | + | − | + | + | − | − | + | ± | + | + |
| n-$C_{12}H_{25}$—S(O)(O)—CH=CH—$CH_2OSO_3Na$ | − | + | + | − | + | + | − | − | + | − | + | + |
| n-$C_{12}H_{25}$—S(O)(O)—CH=CH—$CH_2OPO_3Na_2$ | | | | | | | | | | | | |
| Potassium sorbate | ± | + | + | ± | + | + | − | − | + | + | + | + |
| Sodium dehydroacetate | − | − | + | − | + | + | − | − | + | − | − | + |

EXAMPLE 6

0.2 wt. % of a compound of the present invention and 1.0 wt. % of a commercial antiseptic were added to a typical emulsion-type cutting oil (90 parts of liquid paraffin, 8 parts of sodium dodecylbenzenesulfonate temperature of 30° C. After a predetermined period of time, the number of the microbes per ml of the test solution was counted according to the mixing/dilution test method to determine the antiseptic effect of the compound. The results were as shown in Table 6.

Table 6

| | | Antiseptic effect Test period | | | |
|---|---|---|---|---|---|
| Active compound | Conc. (%) | Immediately after | After 4 days | After 8 days | After 30 days |
| n-$C_{12}H_{25}$—S—CH=$CHCH_2OSO_3Na$ | 0.20 | 225 × $10^3$ | 113 × $10^3$ | 114 × $10^3$ | 57 × $10^3$ |
| n-$C_{12}H_{25}$—S(O)—CH=$CHCH_2OSO_3Na$ | 0.20 | 193 × $10^3$ | 101 × $10^3$ | 64 × $10^3$ | 21 × $10^3$ |
| n-$C_{12}H_{25}$—S(O)(O)—CH=$CHCH_2OSO_3Na$ | 0.20 | 214 × $10^3$ | 67 × $10^3$ | 35 × $10^3$ | 12 × $10^3$ |
| n-$C_{12}H_{25}$—S—CH=$CHCH_2OPO_3Na_2$ | 0.20 | 358 × $10^3$ | 228 × $10^3$ | 121 × $10^3$ | 116 × $10^3$ |
| n-$C_{12}H_{25}$—S(O)—CH=$CHCH_2OPO_3Na_2$ | 0.20 | 253 × $10^3$ | 143 × $10^3$ | 72 × $10^3$ | 28 × $10^3$ |
| n-$C_{12}H_{25}$—S(O)(O)—CH=$CHCH_2OPO_3Na_2$ | 0.20 | 279 × $10^3$ | 117 × $10^3$ | 58 × $10^3$ | 29 × $10^3$ |
| C₆H₅—COONa (reference) | 1.00 | 1203 × $10^3$ | 1321 × $10^3$ | 1248 × $10^3$ | 1097 × $10^3$ |
| 2-hydroxy-C₆H₄—COONa (reference) | 1.00 | 938 × $10^3$ | 807 × $10^3$ | 651 × $10^3$ | 712 × $10^3$ |

Table 6-continued

| Active compound | Conc. (%) | Antiseptic effect Test period | | | |
|---|---|---|---|---|---|
| | | Immediately after | After 4 days | After 8 days | After 30 days |
| Antiseptic not added | — | $3019 \times 10^3$ | $4208 \times 10^3$ | $2436 \times 10^3$ | $2714 \times 10^3$ |

EXAMPLE 7

The emulsifying effects and the antiseptic effects of the following compositions were examined:

Composition A (control): Cutting oil comprising 90 parts of liquid paraffin, 2 parts of sodium salts of fatty acids and 8 parts of sodium dodecylbenzenesulfonate;

Composition B: The same as Composition A except that sodium dodecylbenzenesulfonate was replaced with 8 parts of sodium β-n-dodecylsulfinylallyl alcohol sulfate;

Composition C: The same as Composition A except that sodium dodecylbenzenesulfonate was replaced with 8 parts of sodium β-n-dodecylsulfinylallyl alcohol phosphate; and Composition D: comprising 90 parts of liquid paraffin, 5 parts of sodium dodecylbenzenesulfonate and 5 parts of sodium β-n-dodecylsulfinylallyl alcohol sulfate.

The antiseptic effect was determined by taking one platinum loopful of a sample solution obtained in the same manner as in Example 6, inoculating the same into a bouillon, culturing the same at 30° C. for 48 hours and evaluating the effect of the basis of the turbidity of the liquid. The emulsifying effect was determined by placing a sample in a Ukena tube, shaking the same for a predetermined period of time and evaluating the emulsifying effect from the volume of the substance separated out in a given period of time. The results were as shown in Table 7.

EXAMPLE 8

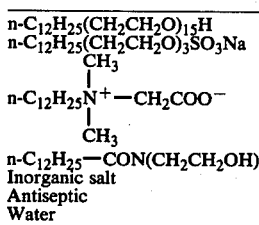

| n-C$_{12}$H$_{25}$(CH$_2$CH$_2$O)$_{15}$H | 10% |
|---|---|
| n-C$_{12}$H$_{25}$(CH$_2$CH$_2$O)$_3$SO$_3$Na | 5 |
| n-C$_{12}$H$_{25}$N$^+$(CH$_3$)$_2$—CH$_2$COO$^-$ | 1 |
| n-C$_{12}$H$_{25}$—CON(CH$_2$CH$_2$OH)$_2$ | 2 |
| Inorganic salt | 1.5 |
| Antiseptic | Given amount (see Table 8) |
| Water | Remainder |

A liquid kitchen detergent of the above composition was formulated to contain a predetermined amount of a compound of the present invention or a commercial antiseptic. A microbial solution was inoculated into the liquid detergent in a proportion of 1 ml:100 ml and the same was subjected to shaking culture at a constant temperature of 30° C. The microbial solution used was prepared by inoculating microbes collected from several portions in a detergent manufacturing plant into a liquid detergent of the same composition as above except that no antiseptic was added and culturing the same until the cell count was $10^7$/ml. The antiseptic effects were determined by taking one platinum loopful of the sample solution, inoculating the same into a bouillon and evaluating the turbidity.

+: Propagation of bacteria

Table 7

| Cutting oil | Conc. | Antisiptic effect Test period | | | | State of emulsion |
|---|---|---|---|---|---|---|
| | | Immediately after | After 4 days | After 8 days | After 30 days | |
| Composition A | 1/20 | ++ | ++ | ++ | ++ | — |
| Composition B | 1/20 | + | — | — | — | State of emulsion is slightly inferior to Composition A but is usable. |
| Composition C | 1/20 | + | ± | — | — | Inferior to Composition B and slightly difficultly usable. |
| Composition D | 1/20 | + | ± | — | — | State of emulsion is equivalent to that of Composition A. |

±: Bacteristatic action
—: Bactericidal action

The results were as shown in Table 8.

Table 8

| Antiseptic | Conc. (%) | Antiseptic effect Test period | | | |
|---|---|---|---|---|---|
| | | After 1 day | After 5 days | After 15 days | After 30 days |
| n-C$_4$H$_9$—S(=O)—CH=CH—CH$_2$OH | 0.3 | — | — | — | — |
| n-C$_4$H$_9$—S(=O)—CH=CH—CH$_2$OSO$_3$Na | 1.0 | + | + | ± | — |
| n-C$_4$H$_9$—S(=O)—CH=CH—CH$_2$OPO$_3$Na$_2$ | 1.5 | + | ± | — | — |
| n-C$_4$H$_9$—S(=O)—CH=CH—CH$_2$OCOCH$_3$ | 0.25 | — | — | — | — |

Table 8-continued

| Antiseptic | Conc. (%) | Antiseptic effect Test period | | | |
|---|---|---|---|---|---|
| | | After 1 day | After 5 days | After 15 days | After 30 days |
| $n\text{-}C_4H_9\text{-}\underset{\underset{O}{\|\|}}{S}\text{-}CH=CH\text{-}CH_2O(CH_2CH_2O)_5H$ | 0.50 | ± | − | − | − |
| | 1.0 | + | − | − | − |
| $n\text{-}C_{12}H_{25}\text{-}\underset{\underset{O}{\|\|}}{S}\text{-}CH=CH\text{-}CH_2O(CH_2CH_2O)_{15}H$ | 1.0 | + | + | + | + |
| COONa-phenyl (reference) | 1.0 | + | + | + | + |
| COONa, OH-phenyl (reference) | 1.0 | + | + | + | + |
| Antiseptic not added | | − | + | + | + | + |

EXAMPLE 9

A hair rinse of the following composition was prepared and the antiseptic effects were determined according to the same test method as described in Example 8.

| | |
|---|---|
| Dipalmityldimethylammonium Chloride | 5 % |
| Liquid paraffin | 5 |
| Glycerol | 10 |
| Sorbitol | 5 |
| Polyoxyethylene(8)lauryl ester | 3 |
| Perfume, colorant | Small amounts |
| Antiseptic | Given amount (see Table 9) |
| Water | Remainder |

The results were as shown in Table 9.

Table 9

| Antiseptic | Conc. (%) | Antiseptic effect Test period | | | Compatibility with the system |
|---|---|---|---|---|---|
| | | After 3 days | After 15 days | After 30 days | |
| $n\text{-}C_4H_9\text{-}\underset{\underset{O}{\|\|}}{S}\text{-}CH=CH\text{-}CH_2OH$ | 0.25 | − | − | − | Compatibility with the system is good. |
| | 0.50 | − | − | − | |
| $n\text{-}C_{12}H_{25}\text{-}\underset{\underset{O}{\|\|}}{S}\text{-}CH=CH\text{-}CH_2OH$ | 0.50 | + | ± | − | " |
| | 1.00 | ± | − | − | |
| $n\text{-}C_4H_9\text{-}\underset{\underset{O}{\|\|}}{S}\text{-}CH=CH\text{-}CH_2OCOC_2H_5$ | 0.25 | ± | − | − | " |
| | 0.50 | − | − | − | |
| $n\text{-}C_4H_9\text{-}\underset{\underset{O}{\|\|}}{S}\text{-}CH=CH\text{-}CH_2O(CH_2CH_2O)_5H$ | 0.25 | ± | − | − | Compatibility with the system is good. As surfactant, some contribution to the system is recognized. |
| | 0.50 | − | − | − | |
| $n\text{-}C_{12}H_{25}\text{-}\underset{\underset{O}{\|\|}}{S}\text{-}CH=CH\text{-}CH_2O(CH_2CH_2O)_{15}H$ | 0.50 | + | + | − | As surfactant, contribution to the system is remarkable. |
| | 1.00 | + | ± | − | |
| $n\text{-}C_4H_9\text{-}\underset{\underset{O}{\|\|}}{S}\text{-}CH=CH\text{-}CH_2O(CH_2\underset{\underset{CH_3}{\|}}{CH}O)_5H$ | 0.25 | + | + | ± | Compatibility is good. Some contribution to the system as surfactant is recognized. |
| | 0.50 | + | + | − | |
| $\left[n\text{-}C_{12}H_{25}\text{-}\underset{\underset{CH_3}{\|}}{\overset{\overset{CH_3}{\|}}{N}}\text{-}CH_2\text{-}C_6H_5\right]^+ Cl^-$ (reference) | 0.20 | + | + | + | The system is separated and the liquid is turbid. This is remarkable in conc. of 0.50%. |
| | 0.50 | + | + | + | |
| $(n\text{-}C_8H_{17}NHCH_2CH_2)_2N^+HCH_2COO^-$ (reference) | 0.20 | + | + | + | the system becomes milky and is unstable |
| | 0.50 | + | + | + | |
| $n\text{-}C_{12}H_{25}\text{-}NH\text{-}\underset{\underset{NH}{\|\|}}{C}\text{-}CH_2$ (reference) | 0.20 | + | + | + | The system is separated. |
| | 0.50 | + | + | + | |

Table 9-continued

| Antiseptic | Conc. (%) | Antiseptic effect Test period | | | Compatibility with the system |
|---|---|---|---|---|---|
| | | After 3 days | After 15 days | After 30 days | |
| HO—⟨benzene⟩—COOC$_2$H$_5$  (reference) | 0.20 | + | + | + | The system becomes turbid remarkably. |
| | 0.50 | + | + | + | |

EXAMPLE 10

To the following hair-treating composition was added a compound of the present invention or a commercial antiseptic in a predetermined concentration to obtain a sample. The antiseptic power was tested as follows: Dust and dirt collected from walls, floors, machines and the air in a cosmetic manufacturing plant were inoculated into a sample of the hair treating composition free of the antiseptic, and the same was stirred continuously with a stirrer to obtain hair-treating composition contaminated with microbes (number of microbes being $10^6$–$10^7$/g). This contaminated composition was inoculated into the test sample in a proportion of 1 g:100 g. Thereafter, the sample was stirred continuously with a stirrer. One platinum loopful of the sample was taken at certain intervals, inoculated into the bouillon and cultured in a constant temperature room at 30° C. for 48 hours. The antiseptic power was determined on the basis of the turbidity of the bouillon culture liquid.

Hair-treating composition:

| Liquid paraffin | 10% |
|---|---|
| Petroleum jelly | 3 |
| Bees wax | 5 |
| Lanolin | 2 |
| Polyoxyethylenesorbitan monostearate | 3 |
| Sorbitan monostearate | 2 |
| Colorant, perfume | Small amounts |
| Antiseptic | Given amount (see Table 10) |
| Water | Remainder |

The results are shown in Table 10.
+: Propagation of bacteria
±: Bacteristatic action
—: Bactericidal action Table 10

| Antiseptic | Conc. (%) | Antiseptic effect Test Period | | | Compatibility with the system |
|---|---|---|---|---|---|
| | | After 7 days | After 15 days | After 30 days | |
| n-C$_4$H$_9$—S—CH=CH—CH$_2$OH | 0.50 | + | + | + | Compatibility with the system is good. |
| | 1.00 | + | — | — | |
| n-C$_4$H$_9$—S(=O)—CH=CH—CH$_2$OH | 0.20 | — | — | — | " |
| | 0.50 | — | — | — | |
| n-C$_4$H$_9$—S(=O)(=O)—CH=CH—CH$_2$OH | 0.20 | + | ± | — | " |
| | 0.50 | — | — | — | |
| n-C$_{12}$H$_{25}$—S(=O)—CH=CH—CH$_2$OH | 0.20 | + | + | — | " |
| | 0.50 | + | — | — | |
| n-C$_4$H$_9$—S(=O)—CH=CH—CH$_2$OCOCH$_3$ | 0.20 | — | — | — | " |
| | 0.50 | — | — | — | |
| n-C$_4$H$_9$—S(=O)—CH=CH—CH$_2$O(CH$_2$CH$_2$O)$_5$H | 0.20 | ± | — | — | Compatibility with the system is good. Some contribution to the emulsification is observed. |
| | 0.50 | — | — | — | |
| n-C$_{12}$H$_{25}$—S(=O)—CH=CH—CH$_2$O(CH$_2$CH$_2$O)$_{15}$H | 0.20 | + | + | + | Compatibility with the system is good. Emulsifying power is excellent. Contribution to the system is great. |
| | 0.50 | + | ± | — | |
| HO—⟨benzene⟩—COOC$_2$H$_5$  (reference) | 0.20 | + | + | + | At a conc. not less than 0.30% small particles are precipitated in the system. |
| | 0.40 | + | + | + | |
| ⟨benzene⟩—COONa  (reference) | 0.20 | + | + | + | The emulsion has a poor stability. This is remarkable at a conc. of 0.50%. |
| | 0.50 | + | + | + | |

Table 10-continued

| Antiseptic | | Conc. (%) | Antiseptic effect Test Period After 7 days | After 15 days | After 30 days | Compatibility with the system |
|---|---|---|---|---|---|---|
| 2-hydroxybenzoate sodium (COONa, OH on benzene) (reference) | | 0.20 | + | + | + | Small particles are precipitated in the system. |
| | | 1.05 | + | ± | − | |
| 2-hydroxybiphenyl (OH on biphenyl) (reference) | | 0.20 | + | + | + | The antiseptic is precipitated due to poor solubility. The emulsion has a poor stability. |
| | | 0.50 | + | + | + | |
| [n-C$_{14}$H$_{29}$—N(CH$_3$)$_2$—CH$_2$—C$_6$H$_5$]$^+$ Cl$^-$ (reference) | | 0.20 | ± | − | − | The emulsion is destroyed and separation thereof is recognized. |
| | | 0.50 | − | − | − | |
| n-C$_{12}$H$_{25}$NH(CH$_2$)$_2$NH(CH$_2$)$_2$NHCH$_2$COOH (reference) | | 0.20 | + | + | + | " |
| | | 0.50 | + | + | + | |

EXAMPLE 11

To a paste of the following composition was added a compound of the present invention or a commercial antiseptic in a predetermined concentration to obtain a sample.

Dirt collected at several portions of a manufacturing plant were inoculated into a paste having the same composition, but free of the antiseptic, to obtain a contaminated paste, which was used as microbial liquid for inoculation.

The microbial liquid was inoculated into a test sample in a ratio of 1 g:100 g. The mixture was placed in a desiccator having a humidity above 90% and allowed to stand at room temperature for two months. The antiseptic power was evaluated from the observed change in appearance, discoloration and odor.

| Paste Composition A | |
|---|---|
| Polyvinyl acetate | 80% |
| Silicon | 5 |
| Phthalate | 2 |
| Perfume | Small amount |
| Dye | Small amount |
| Antiseptic | Given amount (see Table 11) |
| Water | Remainder |

| Paste Composition B | |
|---|---|
| Modified starch | 15 % |
| Polyvinyl acetate | 20 |
| Silicon | 1 |
| Perfume | Small amount |
| Dye | Small amount |
| Antiseptic | Given amount (see Table 11) |
| Water | Remainder |

| Paste Composition C | |
|---|---|
| Modified starch | 40 % |
| Silicon | 1 |
| Urea | 3 |
| Sodium p-toluenesulfonate | 2 |
| Perfume | Small amount |
| Dye | Small amount |
| Antiseptic | Given amount (see Table 11) |
| Water | Remainder |

The results were as shown in Table 11.

Table 11

| Active compound | Conc. (%) | Antiseptic effect Paste composition A | B | C |
|---|---|---|---|---|
| n-C$_8$H$_{17}$—S—CH=CH—CH$_2$OH | 0.50 | | | Δ |
| n-C$_8$H$_{17}$—S(=O)—CH=CH—CH$_2$OH | 0.50 | | | Δ |
| n-C$_8$H$_{17}$—S(=O)(=O)—CH=CH—CH$_2$OH | 0.50 | | Δ | X |
| n-C$_8$H$_{17}$—S(=O)—CH=CH—CH$_2$O(CH$_2$CH$_2$O)$_2$H | 0.50 | | Δ | X |

Table 11-continued

| Active compound | Conc. (%) | Antiseptic effect Paste composition | | |
|---|---|---|---|---|
| | | A | B | C |
| n-C$_8$H$_{17}$—S(=O)—CH=CH—CH$_2$OCOCH$_3$ | 0.50 | | | |
| n-C$_8$H$_{17}$—S(=O)—CH=CH—CH$_2$OSO$_3$Na | 0.50 | | Δ | X |
| n-C$_8$H$_{17}$—S(=O)—CH=CH—CH$_2$OPO$_3$Na$_2$ | 0.50 | | Δ | X |
| Potassium sorbate | 0.50 | Δ | X | X |
| Sodium dehydroacetate | 0.50 | | Δ | X |
| Antiseptic not added | — | Δ | X | X |

: No change in appearance, color or odor.
Δ : One of the appearance, color and odor of the composition became bad.
X : All of the appearance, color and odor of the composition became bad.

EXAMPLE 12

A proper bactericidal/disinfecting agent was added to 10 liters of industrial water. The water was then circulated day and night continuously with a circulating pump. A transparency and odor of the water were observed at certain intervals to determine the bactericidal/disinfecting effect. The transparency of the water was measured with a turbidimeter.

The results were as shown in Table 12.

Table 12

| Bactericidal/disinfecting agent | Conc. | Bactericidal/disinfecting effect | | | | | |
|---|---|---|---|---|---|---|---|
| | | After 15 days | | After 30 days | | After 60 days | |
| | | Transparency | Odor | Transparency | Odor | Transparency | Odor |
| n-C$_3$H$_7$—S(=O)—CH=CH—CH$_2$OH 2% solution | 1/100 | — | — | — | — | — | — |
| | 1/500 | | | | | ± | ± |
| | 1/1000 | — | — | ± | ± | + | + |
| n-C$_3$H$_7$—S(=O)—CH=CHCH$_2$(CH$_2$CH$_2$O)$_2$H 2% solution | 1/100 | — | — | — | — | — | — |
| | 1/500 | — | | — | — | + | ± |
| | 1/1000 | — | — | ± | ± | + | + |
| [n-C$_{14}$H$_{25}$—N(CH$_3$)(CH$_3$)—CH$_2$—C$_6$H$_5$]$^+$ Cl$^-$ (reference) 2% solution | 1/100 | — | — | — | — | — | — |
| | 1/500 | — | — | ± | — | + | ± |
| | 1/100 | + | + | + | + | + | + |
| NaOCl 2% solution (reference) | 1/100 | — | — | — | — | + | ± |
| | 1/500 | — | — | + | ± | + | + |
| | 1/1000 | ± | ± | + | + | + | + |

Palmitylbenzyldimethylammonium chloride caused foaming during the circulation and is questionable for use as a bactericidal/disinfecting agent for water. Sodium hypochlorite was deactivated by the sunlight and the effect thereof did not last for a sufficiently long time. On the other hand, the agents of the present invention did not foam and lasted a long time.

The formula (I) compounds possess antimicrobial activity against one or more of bacteria, fungi and yeasts. They are useful in the same way as various known preservatives, such as lower alkyl esters of p-hydroxy benzoic acid, sodium salicylate and the like. They can be used to preserve various different perishable organic materials against attack and destruction by bacteria, fungi and yeast. Materials requiring such preservation are based on carbohydrates and proteins and various industrial and cosmetic compositions containing fats, oils, waxes and organic surfactants. The invention is based on the discovery of the antimicrobial activity of the formula I and their compatibility with other ingredients of cosmetics, detergent and cutting oil compositions. The other ingredients of the compositions can be any conventional ingredients used in the customary amounts.

The embodiments of the invention in which an exclusive property or privilege is claimed are defined as follows:

1. The method for minimizing deterioration of a non-pharmaceutical and non-food composition containing organic materials that are subject to attack and destruction by micro-organisms, which comprises adding to and blending in said composition a compound or a mixture of compounds having the formula $$R_1—X—CH=CH—CH_2O—Y$$

wherein R$_1$ is alkyl containing 1 to 20 carbon atoms or alkenyl containing 2 to 20 carbon atoms, X is S, SO or SO$_2$, and Y is hydrogen, alkanoyl containing 2 to 20 carbon atoms, alkenoyl containing 3 to 20 carbon atoms, SO₃M or PO₃M₂ wherein M is hydrogen, alkali metal or alkaline earth metal, or (R₂O)ₙH wherein R₂ is ethylene or propylene and n is from 1 to 20, in an amount effective to prevent or retard multiplication of micro-organisms in said composition.

2. The method according to claim 1 wherein said composition comprises one or a mixture of substances subject to deterioration by micro-organisms and selected from the group consisting of carbohydrate, protein, fat, oil, wax and an organic surfactant.

3. The method according to claim 1 in which said composition is a liquid, cream or paste cosmetic composition.

4. The method according to claim 1 wherein R₁ is alkyl containing 1 to 8 carbon atoms or alkenyl containing 2 to 8 carbon atoms and the amount of said compound is from 0.05 to 5 wt. %, based on the total weight of the composition.

5. The method according to claim 1 wherein R₁ is alkyl or alkenyl containing 6 to 20 carbon atoms and the amount of said compound is from 1 to 25 wt.%, based on the total weight of the composition.

6. The method according to claim 1 wherein Y is hydrogen.

7. The method according to claim 1 wherein X is SO and Y is hydrogen, COCH₃, COC₂H₅, SO₃Na, PO₃Na₂ or (R₂O)ₙH.

8. The method according to claim 1 in which X is SO.

9. In a liquid, cream or paste cosmetic composition containing perishable organic materials subject to attack by micro-organisms, and containing a preservative effective to prevent growth of micro-organisms responsible for deterioration of the composition, the improvement which comprises; said preservative is a compound or a mixture of compounds having the formula

R₁—X—CH=CH—CH₂O—Y wherein R₁ is alkyl containing 1 to 20 carbon atoms or alkenyl containing 2 to 20 carbon atoms, X is S, SO or SO₂, and Y is hydrogen, alkanoyl containing 2 to 20 carbon atoms, alkenoyl containing 3 to 20 carbon atoms, SO₃M or PO₃M₂ wherein M is hydrogen, alkali metal or alkaline earth metal, or (R₂O)ₙH wherein R₂ is ethylene or propylene and n is from 1 to 20, and is present in an amount effective to prevent or retard multiplication of micro-organisms in said composition.

10. A cosmetic composition according to claim 9 wherein X is SO and Y is hydrogen, COCH₃, COC₂H₅, SO₃Na, PO₃Na₂ or (R₂O)ₙH.

11. A composition according to claim 9 wherein R₁ is alkyl containing 1 to 8 carbon atoms or alkenyl containing 2 to 8 carbon atoms, and the amount of said compound is from 0.05 to 5 wt. %, based on the total weight of the composition.

12. A composition according to claim 9 wherein R₁ is alkyl or alkenyl containing 6 to 20 carbon atoms, and the amount of said compound is from 1 to 25 wt. %, based on the total weight of the composition.

* * * * *